(12) United States Patent
Saenz Villalobos et al.

(10) Patent No.: US 11,484,317 B2
(45) Date of Patent: Nov. 1, 2022

(54) MULTIPLE BAND LIGATION

(71) Applicant: BOSTON SCIENTIFIC SCIMED, INC., Maple Grove, MN (US)

(72) Inventors: Gonzalo Jose Saenz Villalobos, Heredia (CR); Kevin McEvilly, Galway (IE); Alejandro Brenes Acosta, San Jose (CR); Daniel Calvo Camacho, Ciudad Colon (CR); Rafael Berenzon, La Union (CR); Esteban Solano Montenegro, Heredia (CR); Diana Catalina Rodriguez Forero, San Jose (CR); Daniel Eduardo Mata Barrantes, San Isidro (CR); Jose Pablo Nunes Corella, San Jose (CR); Viviana Artavia Salas, Alajuela (CR)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 267 days.

(21) Appl. No.: 16/905,707

(22) Filed: Jun. 18, 2020

(65) Prior Publication Data

US 2021/0007748 A1     Jan. 14, 2021

Related U.S. Application Data

(60) Provisional application No. 62/871,348, filed on Jul. 8, 2019.

(51) Int. Cl.
*A61B 17/12* (2006.01)
*A61B 17/00* (2006.01)

(52) U.S. Cl.
CPC .......... *A61B 17/12013* (2013.01); *A61B 2017/00561* (2013.01); *A61B 2017/12018* (2013.01)

(58) Field of Classification Search
CPC .... A61B 2017/12018; A61B 17/12009; A61B 2017/3452; A61B 17/12013; A61B 17/12; A61M 2210/1067
See application file for complete search history.

(56) References Cited

U.S. PATENT DOCUMENTS

| 4,257,419 | A | 3/1981 | Goltner et al. |
| 7,488,333 | B2 | 2/2009 | Ghareeb |
| 9,693,778 | B2 | 7/2017 | Kamler |
| 2002/0111639 | A1 | 8/2002 | Armstrong |
| 2010/0042110 | A1 | 2/2010 | Kelley et al. |
| 2018/0317923 | A1* | 11/2018 | Robbins ........... A61B 17/12009 |
| 2019/0328397 | A1 | 10/2019 | Nguyenba et al. |

* cited by examiner

*Primary Examiner* — Katherine H Schwiker
*Assistant Examiner* — Serenity A Miller
(74) *Attorney, Agent, or Firm* — Fay Kaplun & Marcin, LLP

(57) ABSTRACT

A device includes a housing having a first opening for receiving tissue therein and a distal head disposed at least partly within the housing. The distal head is configured to rotate about a longitudinal axis of the distal head. The device also includes a first holding member coupled to the housing and a second holding member coupled to the distal head. The first and second holding members are configured so that rotating the distal head stretches a first ligation band coupled to the first and second holding members, permitting tissue drawn into the first opening to pass through an opening of the first ligation band.

23 Claims, 4 Drawing Sheets

MULTIPLE BAND LIGATION

PRIORITY CLAIM

The present disclosure claims priority to U.S. Provisional Patent Application Ser. No. 62/871,348 filed Jul. 8, 2019; the disclosure of which is incorporated herewith by reference.

FIELD

The present disclosure relates to the treatment of hemorrhoids and, in particular, relates to a device for ligating hemorrhoids using multiple ligation bands and holding members to draw in hemorrhoid tissue.

BACKGROUND

Hemorrhoids, swollen and inflamed veins around the anus or in the lower rectum, may be external, forming under the skin around the anus, or internal, forming in the lining of the anus and the lower rectum. Approximately 50% of adults over 50 years of age in the United States have experienced symptoms, including bleeding, irritation or pain, due to hemorrhoids.

Hemorrhoid cases are sometimes treated non-surgically. Some common methods include rubber band ligation (RBL), infrared coagulation (IRC), HET™ Bipolar, or topical treatments. RBL systems operate by placing a rubber band at the base of the hemorrhoid, strangulating blood flow to reduce inflammation and, eventually, eliminating the hemorrhoid.

Many adults may have more than one hemorrhoid. For example, in adult men, there are three common sites for internal hemorrhoids: the right anterior, the left lateral, and the right posterior of the rectum. It is desirable to treat multiple internal hemorrhoids in a single, minimally invasive procedure.

SUMMARY

The present disclosure relates to a device comprising a housing having a first opening for receiving tissue therein and a distal head disposed at least partly within the housing. The distal head is configured to rotate about a longitudinal axis of the distal head. The device comprises a first holding member coupled to the housing and a second holding member coupled to the distal head. The first and second holding members are configured so that rotating the distal head stretches a first ligation band coupled to the first and second holding members, permitting tissue drawn into the first opening to pass through an opening of the first ligation band.

In an embodiment, the housing has a second opening and a third holding member coupled to the housing adjacent to the second opening and a fourth holding member coupled to the head, the third and fourth holding members configured so that rotating the distal head stretches a second ligation band coupled to the third and fourth holding members to permit tissue drawn into the second opening to pass through an opening of the second ligation band.

In an embodiment, the housing has a third opening and a fifth holding member coupled to the housing adjacent to the third opening and a sixth holding member coupled to the head, the fifth and sixth holding members configured so that rotating the distal head stretches a third ligation band coupled to the fifth and sixth holding members to permit tissue drawn into the third opening to pass through an opening of the third ligation band.

In an embodiment, the first, second and third openings are spaced about a circumference of a conical distal portion of the housing and rotating the distal head stretches the first, second and third ligation bands substantially simultaneously.

In an embodiment, at least one of the first and second holding members is structured to break when the distal head is rotated by a predetermined amount to release a ligation band coupled thereto from the device.

In an embodiment, one of the housing and the distal head includes an interfering member which, during rotation of the head relative to the housing, contacts the one of the first and second holding members so that further rotation of the head relative to the housing breaks the one of the first and second holding members.

An embodiment further comprises, a rotation mechanism for rotating the distal head relative to the housing and an actuator that remains accessible to a user, the actuator coupled to the rotation mechanism so that operation of the actuator rotates the housing relative to the head.

An embodiment further comprises, a vacuum port extending from a proximal end of the housing configured for attachment to a vacuum source, wherein external actuation of the vacuum source induces a vacuum at the distal head for drawing the tissue into the first opening.

In an embodiment, the distal head defines a first recessed portion sized to receive a portion of the tissue prior to rotating the distal head and a first pathway portion adjacent to the first recessed portion sized to receive a greater portion of the tissue after rotating the distal head.

In an embodiment, the first pathway portion is inclined so that, when the device is drawn proximally, the received tissue passes out of the first opening.

The present disclosure also relates to a method comprising receiving tissue through a first opening in a housing of a device, the device having a distal head disposed at least partly within the housing and configured to rotate about a longitudinal axis of the distal head. The device comprises a first holding member coupled to the housing and a second holding member coupled to the distal head. The method includes rotating the distal head so that a first ligation band coupled to the first and second holding members is stretched to permit tissue drawn into the first opening to pass through an opening of the first ligation band.

In an embodiment, the housing has a second opening and a third holding member coupled to the housing adjacent to the second opening and a fourth holding member coupled to the head, the third and fourth holding members configured so that rotating the distal head stretches a second ligation band coupled to the third and fourth holding members to permit tissue drawn into the second opening to pass through an opening of the second ligation band.

In an embodiment, the housing has a third opening and a fifth holding member coupled to the housing adjacent to the third opening and a sixth holding member coupled to the head, the fifth and sixth holding members configured so that rotating the distal head stretches a third ligation band coupled to the fifth and sixth holding members to permit tissue drawn into the third opening to pass through an opening of the third ligation band.

In an embodiment, the first, second and third openings are spaced about a circumference of a conical distal portion of the housing and rotating the distal head stretches the first, second and third ligation bands substantially simultaneously.

In an embodiment, at least one of the first and second holding members is structured to break when the distal head is rotated by a predetermined amount to release a ligation band coupled thereto from the device.

In an embodiment, one of the housing and the distal head includes an interfering member which, during rotation of the head relative to the housing, contacts the one of the first and second holding members so that further rotation of the head relative to the housing breaks the one of the first and second holding members.

In an embodiment, the device has a rotation mechanism for rotating the distal head relative to the housing and an actuator coupled to the rotation mechanism so that operation of the actuator rotates the housing relative to the head.

An embodiment further comprises, externally actuating a vacuum source attached to a vacuum port extending from a proximal end of the housing, wherein the external actuation of the vacuum source induces a vacuum at the distal head for drawing the tissue into the first opening.

In an embodiment, the distal head defines a first recessed portion sized to receive a portion of the tissue prior to rotating the distal head and a first pathway portion adjacent to the first recessed portion sized to receive a greater portion of the tissue after rotating the distal head.

In an embodiment, the first pathway portion is inclined so that, when the device is drawn proximally, the received tissue passes out of the first opening.

BRIEF DESCRIPTION

DETAILED DESCRIPTION

Figure 1:
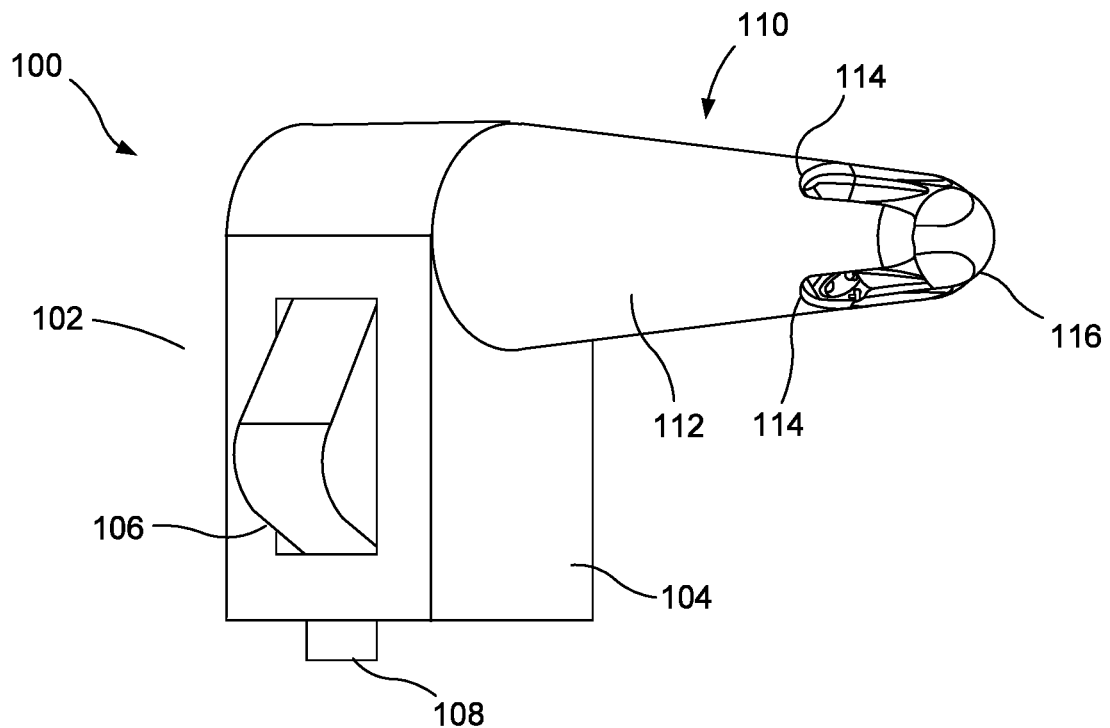
FIG. 1 shows a perspective view of a device for ligating hemorrhoids according to an exemplary embodiment of the present disclosure.
Figure 2:
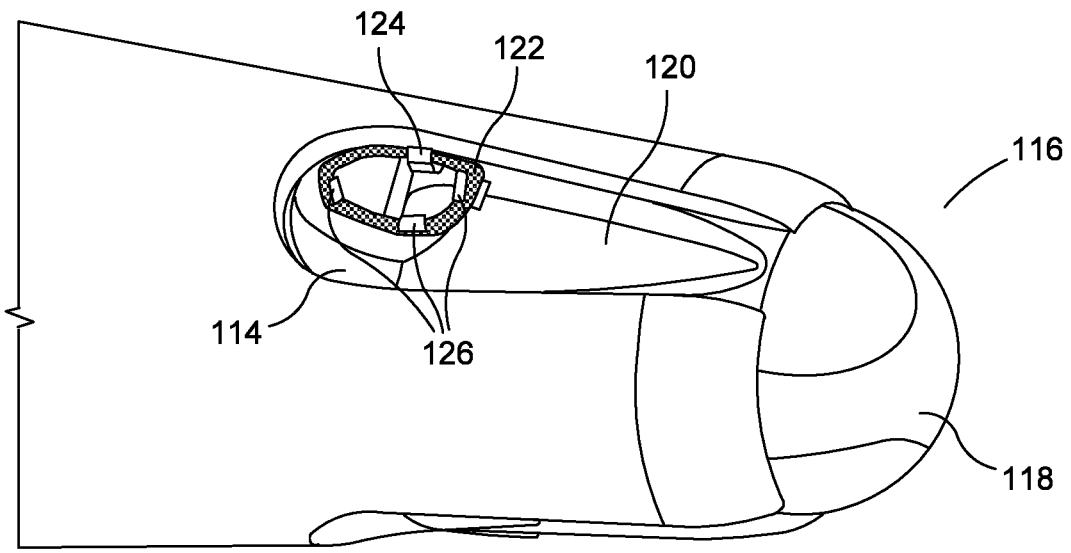
FIG. 2 shows a perspective view of a head of the device of FIG. 1.
Figure 3:
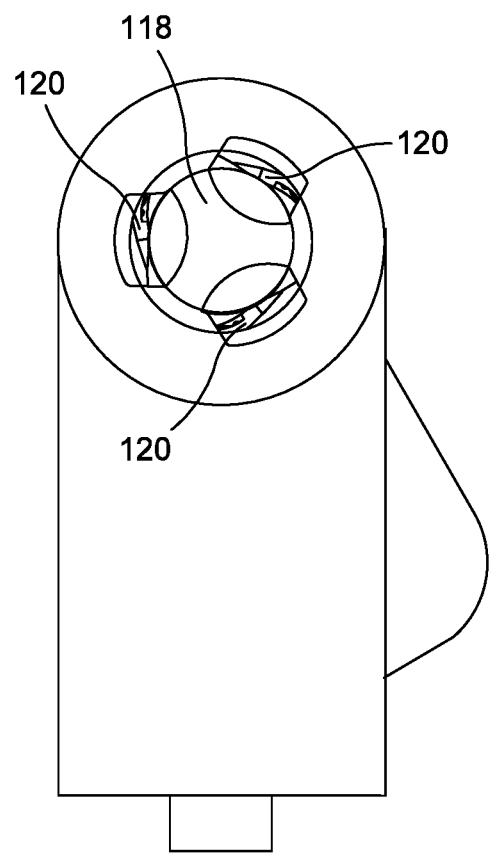
FIG. 3 shows a front view of cavities of the head of the device of FIG. 1.

The present disclosure may be further understood with reference to the following description and the appended drawings, wherein like elements are referred to with the same reference numerals. The present disclosure is directed to a multiple band ligation device for ligating one hemorrhoid or multiple hemorrhoids simultaneously. Exemplary embodiments of the present disclosure describe a gun-shaped device comprising a handle and a conical portion comprising a distal head defining a plurality of hemorrhoid receiving cavities. The device applies a ligation band to each hemorrhoid received in one of the cavities and releases the hemorrhoids to free the device for repositioning or removal from the body. It should be noted that the exemplary embodiments are described herein as a device with three hemorrhoid receiving cavities for simultaneous or serial ligation of up to three hemorrhoids without reloading the device. However, the principles described herein may be applied to a device with more or less than three cavities as would be understood by those skilled in the art. It is further noted that the terms proximal and distal, as used herein, are intended to refer to a direction toward (proximal) and away from (distal) a user of the device.

As shown in FIGS. 1-5, a device 100 for ligating hemorrhoids comprises a proximal handle portion 102 and a conically-shaped distal portion 110. The handle 102 comprises a handle housing 104, a trigger 106 extending outward from the handle housing 104 through an opening in the handle housing 104, and a fitting 108 at the proximal end of the handle 102 for connecting the device 100 to a vacuum source (not shown). The fitting 108 may be, for example, a Luer fitting although any other suitable fitting may be employed as would be understood by those skilled in the art. The vacuum source may, for example, be a dedicated automatic device, such as a pump, or may be a manual device, such as a syringe or any other suitable source. The vacuum source is actuated separately from the actuation mechanism of the device 100, i.e. the trigger 106. The trigger 106 is actuated to advance the device 100 from a first configuration to a second configuration via an internal rotation mechanism (not shown). The exemplary disposition of the trigger 106 on the side of the device 100 is for illustrative purposes only, and the trigger 106 may be disposed on any face of the handle housing 104.

The conically-shaped distal portion 110 comprises a distal housing 112 with distal openings 114. In the first configuration, the distal openings 114 provide access to the cavities 120 defined by a distal head 116. Each of the distal openings 114 may have, on one side, a protrusion 136 extending radially inward from the distal housing 112 partway into the cavity 120, as seen in the cross-sectional views of FIG. 5, and, on the other side, a housing holding ring 124 for holding a ligation band 122 until the band 122 is deployed over a hemorrhoid. The distal head 116 extends longitudinally from a proximal end coupled to the rotation mechanism to a distal end terminating at a rounded distal tip 118. The rotation mechanism may, for example, be any mechanical linkage configured to translate the motion of the trigger into rotational motion to rotate the distal head 116 relative to the distal housing 112. For example, the rotation mechanism may be gear- or pulley-based.

The distal head 116 is configured to rotate within the distal housing 112 while the distal housing 112 remains fixed. In an embodiment, a device 100 may include three cavities 120, and the distal head 116 may be rotatable approximately 60° to advance from the first configuration into the second configuration. However, the extent of the rotation may be more or less than 60°. In the first configuration, the distal head 116 and the distal housing 112 are attached through each of the distal openings 114 by a flexible ligation band 122. The ligation band 122 may be any flexible band that has a natural (unstretched) state of a relatively small diameter and which can withstand stretching to a diameter many times its unstretched diameter. For instance, the ligation band 122 may be a rubber band. The ligation band 122 extends from the housing holding ring 124 on the distal housing 112 to one or more head holding rings 126 on the distal head 116 while the device 100 is in the first configuration. As the distal head 116 rotates the ligation band 122 stretches until the device 100 reaches the second configuration, whereupon the holding rings are broken and the stretched ligation band 122 constricts under its natural bias toward its natural state around the base of a hemorrhoid, as will be discussed further below.

The present disclosure describes a specific embodiment of the device 100 wherein the ligation bands 122 are held by holding rings 124, 126 until the second configuration is reached and the holding rings 124, 126 are broken by interference with device components to release the ligation bands 122. However, the present disclosure is not limited to this specific release mechanism. For example, the ligation bands 122 may be held in place by structures other than holding rings, such as open-ended protrusions. In this example, the bands 122 may be slid off the protrusions by device components. In still another example, a device similar to the device 100 may include movable holding clamps or hooks similar in shape to the holding rings 124, 126 shown in FIGS. 5A to 5D but which differ from these in that the hooks of this device are movable to release the ligating bands. Specifically, the hooks holding the ligating bands in this device do not break to release the ligating band but are moved out of the way of the ligating band (or are simply released to move under force applied by the ligating band) via an actuation mechanism.

Those skilled in the art will understand that such a device may then be sterilized, reloaded with ligating bands and reused. In this example, the bands 122 may be deployed by an independent actuator, such as an external button or trigger, connected to the clamps or hooks via pull wires or another actuation mechanism. Even when the holding rings 124, 126 are implemented in the device 100, the rings 124, 126 may be broken by means other than device component interference. For example, a mechanism may be externally actuated by a user of the device separately from the actuation of the rotation mechanism to break the holding rings.

As may be seen in FIGS. 5A-5D, the distal head 116 comprises a plurality of recessed portions 128 separated by pathway portions 130. Each of the recessed portions substantially defines the limits of a cavity 120 into which a hemorrhoid may be drawn for ligation when the device 100 is in the first configuration. A cavity 120 may be defined as the area substantially bounded by the recessed portion 128 and extending longitudinally from the most proximal point of the distal opening 114 to the distal tip 118, with the exception to a full delimitation of the cavity 120 being a gap 132 that opens to the interior 134 of the device 100.

The interior 134 of the device 100 is in direct air communication with the vacuum source. In one embodiment, tubing extends internal to the device 100 from the proximal fitting 108 to the distal head 116 to minimize the mass of air to be displaced. In another embodiment, the proximal fitting 108 opens to a substantially airtight interior of the device 100 and the vacuum is imposed on the entirety of the mass of air internal to the device. In the first configuration the gap 132 is at its smallest and the ligation band 122 surrounds the gap. As the device 100 advances from the first configuration toward the second configuration and suction is applied, the gap 132 widens permitting a hemorrhoid positioned adjacent to the gap to be drawn by the suction into the interior 134 of the device 100.

FIGS. 5A-5D show the transition of the device 100 into the second configuration from the first configuration. FIG. 5A shows the first configuration, prior to actuation of the trigger 106. The vacuum has been pulled, and a small part of the hemorrhoid has been drawn by the suction into the gap 132 through the center of the opening in the ligation band 122 which is at a minimum stretch level. FIGS. 5B-5C show the device 100 as the distal head 116 rotates. During this rotation the ligation band 122 stretches between the distal head 116 and the housing holding ring 124 allowing more of the hemorrhoid to be drawn through the band 122 and to extend further into the interior 134 of the device 100. FIG. 5D shows the second configuration in which the distal head 116 has been rotated fully. The holding rings 124, 126 may then break at locations marked by X's, and, as shown in FIG. 5D, the ligation band 122 is released to constrict around the base of the hemorrhoid cutting off blood flow to the hemorrhoid. Once the blood flow is cut off, the hemorrhoid may die, and the tissue and band may separate and pass from the patient.

Figure 4:
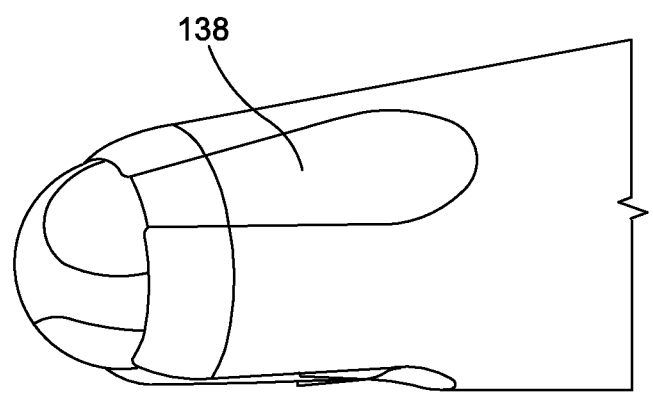
FIG. 4 shows a perspective view of the head of the device of FIG. 1 with a cavity closed.
Figure 5:
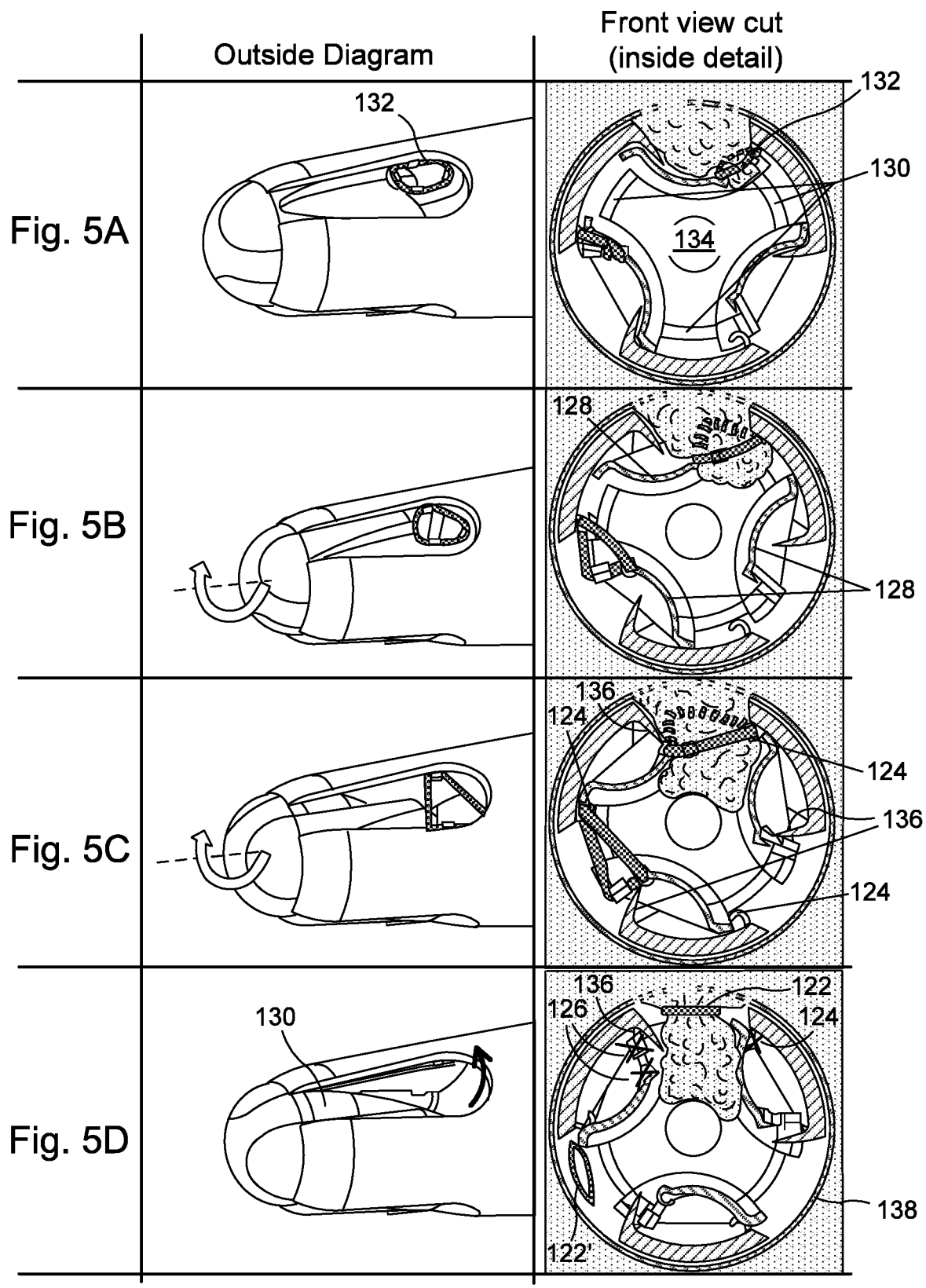
FIGS. 5A-5D show a ligation procedure using the device of FIG. 1.
Figure 6:
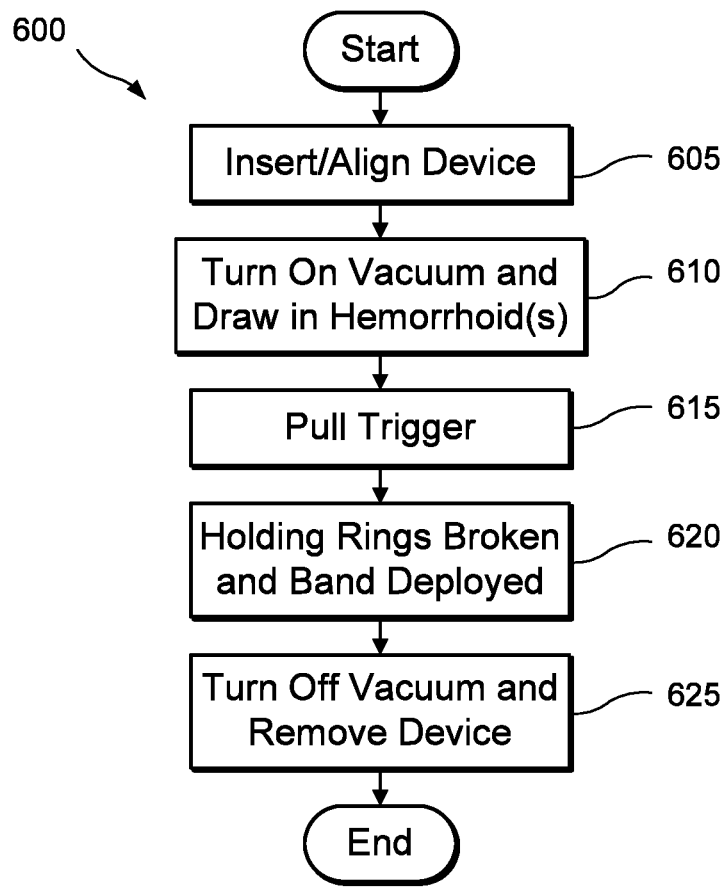
FIG. 6 shows a method for performing the ligation procedure using the device of FIG. 1.

FIG. 6 shows an exemplary method 600 for performing the ligation procedure using the device 100 of FIG. 1. In this embodiment the device 100 has three cavities 120 for treating three hemorrhoids simultaneously. In 605, the device 100 is introduced into the body of the patient in the first configuration, i.e. prior to actuation of the device 100. Upon insertion of the device 100, the cavities 120 of the device 100 are aligned with target hemorrhoids to be treated. The hemorrhoid locations may be known, for example, from a prior examination or may be determined through any known method. All three cavities 120 are utilized at the same time in the procedure when the patient has three hemorrhoids each of which can be roughly aligned with a corresponding one of the cavities 120. When the patient has less than three hemorrhoids total, or less than three hemorrhoids that can be aligned with the cavities 120, a cavity cover 138, as shown in FIG. 4, may be used to prevent non-hemorrhoidal tissue from being pulled by the vacuum and creating lesions. The cavity cover 138 in this embodiment also prevents unused bands from jumping off the device and into the body of the patient as the bands are released from their respective holding rings.

In 610, the vacuum source is actuated remotely from the device. The vacuum source may be an automatic device or a manual device. The partial vacuum resulting from the actuation of the vacuum source draws the hemorrhoid tissue adjacent to each of the uncovered cavities 120 partially through the corresponding gaps 132 toward the interior 134 of the device 100, as shown in FIG. 5A. The remainder of the hemorrhoid (that has not yet been pulled into the interior 134) rests on the recessed portion 128 of the distal head 116 in the cavity 120.

In 615, the trigger 106 is actuated, rotating the distal head 116 toward the second configuration. The recessed portion 128 in the first configuration is aligned with the distal opening 114 of the distal housing 112, thus forming the cavity 120, so that the rotation of the recessed portion 128 away from the distal opening 114 widens the gap 132 leading to the interior of the distal head 116. As shown in FIGS. 5B-5C, the gap 132 gradually becomes subsumed into a distal end of the pathway portion 130 opening directly into the interior 134 of the device. Throughout the rotation, the vacuum pressure draws the hemorrhoidal tissue further into the interior 134 of the device 100.

In 620, the distal head 116 completes rotation to the second configuration and multiple actions occur substantially simultaneously. First, the completion of the rotation permits the hemorrhoids to be drawn as fully as possible into the interior 134 of the device 100, such that the base of each hemorrhoid, or a portion of each hemorrhoid close to its base, is drawn even with the distal opening 114 of the distal housing 112. The vacuum source pulls proximally on the hemorrhoid and the pathway portion 130 naturally slopes toward the proximal end of the device 100. The gap 132, which was relatively small in the first configuration, has become a direct, open path into the interior of the device 100 in the second configuration.

A second action that occurs upon completion of the rotation is the breaking of the holding rings, i.e., the housing holding ring 124 (attached to the distal housing 112) and the head holding rings 126 (attached to the distal head 116). As shown in FIG. 5D, the protrusion 136 extending radially inward from the distal housing 112 interferes with the rotation of the head holding rings 126. The protrusion 136 is structurally stronger than the head holding rings 126 so that further rotation of the head holding rings 126 against the protrusion 136 breaks the head holding rings 126. In a similar manner, the housing holding ring 124 interferes with the rotation of a portion of the recessed portion 128 forming an adjacent cavity. As the recessed portion 128 is structurally stronger than the housing holding ring 124, further rotation of the recessed portion 128 against the housing holding ring 124 breaks the housing holding ring 124.

The breaking of the holding rings 124, 126 releases the ligation bands 122 so that they constrict around the base of each of the hemorrhoids (i.e., the part of the hemorrhoid currently within the diameter of each of the bands 122). Thus, blood flow to the hemorrhoids is effectively cut off. In the event that one or more of the cavities 120 is covered by the cavity covers 138, the breaking of the holding rings 124, 126 frees the corresponding ligation band 122 which is then drawn into the interior 134 of the device 100 so that the band 122 is not released into the body of the patient. As shown in FIG. 5D, band 122' is released by the breaking of holdings rings 124, 126 but, because the corresponding cavity 120 is covered by the cavity cover 138, the band 122' is held in the device 100 and is not released into the body.

Figure 7:
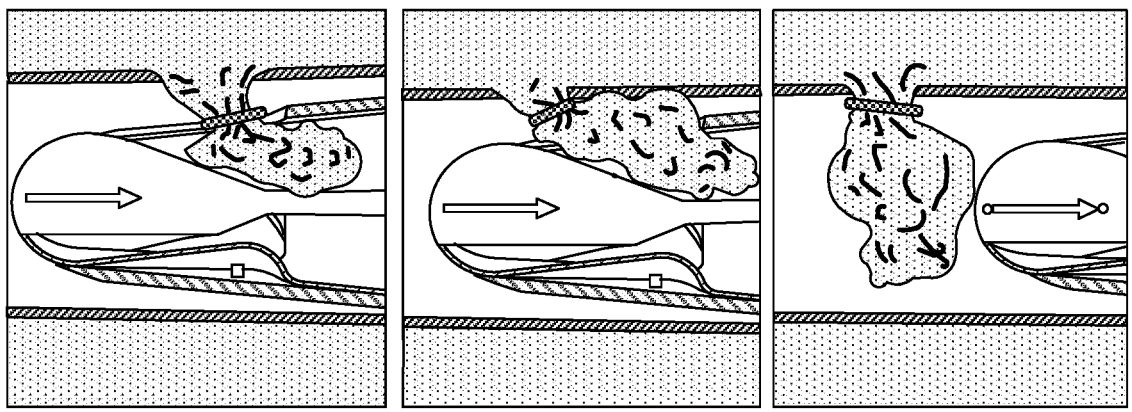
FIG. 7 shows a removal procedure for the device of FIG. 1.

In 625, the vacuum source is deactivated and the device 100 is removed from the patient. The deactivation of the vacuum source allows the hemorrhoid to partially draw back out of the interior 134 of the device 100. As the device 100 is removed from the patient the hemorrhoid is drawn along the pathway portion 130, as shown in FIG. 7, allowing for smooth removal of the hemorrhoids from the device 100. As shown in FIG. 7, those skilled in the art will understand that, in certain cases, it may not be possible to draw all of the hemorrhoid tissue into the device 100, therefore, some hemorrhoid tissue may remain after the ligation procedure.

It may be seen based on the foregoing that the device 100 is intended as a single-use disposable device. The components of the device 100 may be machined metal or molded plastic, with the exception of the holding rings 124, 126 which are required to be breakable and are preferably made from a relatively low strength material such as plastic.

device 100
proximal handle 102
handle housing 104
trigger 106
fitting 108
distal portion 110
distal housing 112
distal openings 114
distal head 116
distal tip 118
cavities 120
ligation bands 122
housing holding ring 124
head holding ring 126
recessed portion 128
pathway portion 130
gap 132
interior 134 of device
protrusion 136
cavity cover 138

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather, modifications are also covered within the scope of the present invention as defined by the appended claims.

The invention claimed is:

1. A device, comprising:
    a housing having a first and a second opening for receiving tissue therein;
    a distal head disposed at least partly within the housing and configured to rotate about a longitudinal axis of the distal head; and
    a first holding member coupled to the housing and a second holding member coupled to the distal head, the first and second holding members configured so that a first ligation band is extendable in response to rotation of the distal head relative to the housing, the first ligation band being coupled to the first and second holding members and;
    a third holding member coupled to the housing adjacent to the second opening and a fourth holding member coupled to the distal head, the third and fourth holding members configured so that rotating the distal head relative to the housing stretches a second ligation band coupled to the third and fourth holding members to permit tissue drawn into the second opening to pass through an opening of the second ligation band.

2. The device of claim 1, wherein the first ligation band is positioned and oriented relative to the first opening to permit tissue drawn into the first opening to pass through an opening of the first ligation band as the first ligation band is extended.

3. The device of claim 1, wherein the housing has a third opening and a fifth holding member coupled to the housing adjacent to the third opening and a sixth holding member coupled to the distal head, the fifth and sixth holding members configured so that rotating the distal head relative to the housing stretches a third ligation band coupled to the fifth and sixth holding members to permit tissue drawn into the third opening to pass through an opening of the third ligation hand.

4. The device of claim 3, wherein the first, second and third openings are spaced about a circumference of a conical distal portion of the housing and rotating the distal head relative to the housing stretches the first, second and third ligation bands substantially simultaneously.

5. The device of claim 1, wherein at least one of the first and second holding members is structured to break when the distal head is rotated relative to the housing by a predetermined amount to release from the device the first a ligation band coupled thereto.

6. The device of claim 5, wherein one of the housing and the distal head includes an interfering member which, during rotation of the distal head relative to the housing, contacts the at least one of the first and second holding members so that further rotation of the distal head relative to the housing breaks the one of the first and second holding members.

7. The device of claim 1, further comprising:
    a rotation mechanism for rotating the distal head relative to the housing; and
    an actuator that remains accessible to a user, the actuator coupled to the rotation mechanism so that operation of the actuator rotates the housing distal head relative to the housing.

8. The device of claim 1, further comprising:
    a vacuum port extending from a proximal end of the housing configured for attachment to a vacuum source, wherein external actuation of the vacuum source induces a vacuum at the distal head for drawing the tissue into the first opening.

9. The device of claim 1, wherein the distal head defines a first recessed portion sized to receive a portion of the tissue prior to rotating the distal head and a first pathway portion adjacent to the first recessed portion sized to receive a greater portion of the tissue after rotating the distal head.

10. The device of claim 9, wherein the first pathway portion is inclined so that, when the device is drawn proximally, the received tissue passes out of the first opening.

11. The device of claim 1, wherein at least one of the first and second holding members is structured to move out of engagement of the first ligation band when the distal head is rotated relative to the housing by a predetermined amount to release from the device the first ligation band.

12. The device of claim 1, wherein at least one of the first and second holding members is structured to move out of engagement with the first ligation band when a corresponding ligation band release actuator is actuated to release from the device the first ligation band.

13. A method, comprising:
receiving tissue through a first opening in a housing of a device, the device having a distal head disposed at least partly within the housing, the distal head being configured to rotate relative to the housing about a longitudinal axis of the distal head, a first holding member coupled to the housing and a second holding member coupled to the distal head; and
rotating the distal head relative to the housing so that a first ligation band coupled to the first and second holding members is stretched.

14. The method of claim 13, wherein the first ligation band is positioned and oriented relative to the first opening to permit tissue drawn into the first opening to pass through an opening of the first ligation band as the first ligation band is stretched.

15. The method of claim 14, wherein the housing has a second opening and a third holding member coupled to the housing adjacent to the second opening and a fourth holding member coupled to the distal head, the third and fourth holding members configured so that rotating the distal head relative to the housing stretches a second ligation band coupled to the third and fourth holding members to permit tissue drawn into the second opening to pass through an opening of the second ligation band.

16. The method of claim 15, wherein the housing has a third opening and a fifth holding member coupled to the housing adjacent to the third opening and a sixth holding member coupled to the distal head, the fifth and sixth holding members configured so that rotating the distal head relative to the housing stretches a third ligation band coupled to the fifth and sixth holding members to permit tissue drawn into the third opening to pass through an opening of the third ligation band.

17. The method of claim 16, wherein the first, second and third openings are spaced about a circumference of a conical distal portion of the housing and rotating the distal head relative to the housing stretches the first, second and third ligation bands substantially simultaneously.

18. The method of claim 13, wherein at least one of the first and second holding members is structured to break when the distal head is rotated relative to the housing by a predetermined amount to release the first ligation band coupled thereto from the device.

19. The method of claim 18, wherein one of the housing and the distal head includes an interfering member which, during rotation of the dital head relative to the housing, contacts the at least one of the first and second holding members so that further rotation of the distal head relative to the housing breaks the one of the first and second holding members.

20. The method of claim 13, wherein the device has a rotation mechanism for rotating the distal head relative to the housing and an actuator coupled to the rotation mechanism so that operation of the actuator rotates the distal head relative to the housing.

21. The method of claim 13, further comprising:
externally actuating a vacuum source attached to a vacuum port extending from a proximal end of the housing, wherein the external actuation of the vacuum source induces a vacuum at the distal head for drawing the tissue into the first opening.

22. The method of claim 13, wherein the distal head defines a first recessed portion sized to receive a portion of the tissue prior to rotating the distal head relative to the housing and a first pathway portion adjacent to the first recessed portion sized to receive a greater portion of the tissue after rotating the distal head relative to the housing.

23. The method of claim 22, wherein the first pathway portion is inclined so that, when the device is drawn proximally, the received tissue passes out of the first opening.

* * * * *